(12) United States Patent
Moore

(10) Patent No.: US 9,326,963 B2
(45) Date of Patent: *May 3, 2016

(54) NUTRITIVE COMPOSITIONS AND METHODS OF USING SAME

(75) Inventor: Eileen Moore, Parma, OH (US)

(73) Assignee: Pentec Health, Inc., Glen Mills, PA (US)

( * ) Notice: Subject to any disclaimer, the term of this patent is extended or adjusted under 35 U.S.C. 154(b) by 277 days.

This patent is subject to a terminal disclaimer.

(21) Appl. No.: 12/498,773

(22) Filed: Jul. 7, 2009

(65) Prior Publication Data

US 2010/0136133 A1 Jun. 3, 2010

Related U.S. Application Data

(60) Provisional application No. 61/078,636, filed on Jul. 7, 2008, provisional application No. 61/080,567, filed on Jul. 14, 2008.

(51) Int. Cl.

| | |
|---|---|
| *A61P 3/02* | (2006.01) |
| *A61K 31/70* | (2006.01) |
| *A61K 38/28* | (2006.01) |
| *A61K 33/42* | (2006.01) |
| *A61K 33/34* | (2006.01) |
| *A61K 33/32* | (2006.01) |
| *A61K 33/06* | (2006.01) |
| *A61K 31/20* | (2006.01) |
| *A61K 31/195* | (2006.01) |
| *A61K 31/7004* | (2006.01) |
| *A61K 45/06* | (2006.01) |

(52) U.S. Cl.
CPC .............. *A61K 31/20* (2013.01); *A61K 31/195* (2013.01); *A61K 31/7004* (2013.01); *A61K 45/06* (2013.01)

(58) Field of Classification Search
CPC . A61K 2300/00; A61K 31/195; A61K 31/20; A61K 31/7004; A61K 45/06
See application file for complete search history.

(56) References Cited

U.S. PATENT DOCUMENTS

| | | | |
|---|---|---|---|
| 4,489,097 A | 12/1984 | Stone | |
| 4,491,589 A | 1/1985 | Dell et al. | |
| 4,604,286 A | 8/1986 | Kawajiri | |
| 4,670,261 A | 6/1987 | Samejima et al. | |
| 5,122,515 A * | 6/1992 | Smith et al. | 514/5.5 |
| 5,278,149 A * | 1/1994 | Provost et al. | 514/23 |
| 5,571,783 A | 11/1996 | Montagne et al. | |
| 5,767,123 A | 6/1998 | Yoshida et al. | |
| 6,610,206 B1 | 8/2003 | Callan et al. | |
| 6,916,424 B2 | 7/2005 | Collins et al. | |
| 7,323,206 B1 | 1/2008 | Driscoll et al. | |
| 7,445,801 B2 | 11/2008 | Faict et al. | |
| 7,670,491 B2 | 3/2010 | Callan et al. | |
| 2004/0209814 A1 * | 10/2004 | Nauck et al. | 514/12 |
| 2005/0148647 A1 * | 7/2005 | Landry | 514/400 |
| 2006/0211631 A1 * | 9/2006 | Mitsumoto et al. | 514/23 |
| 2007/0092579 A1 | 4/2007 | Trouilly et al. | |
| 2007/0196445 A1 | 8/2007 | Abbruzzese et al. | |
| 2008/0255499 A1 * | 10/2008 | Kim | 604/28 |
| 2009/0203626 A1 | 8/2009 | Brand et al. | |
| 2010/0143498 A1 | 6/2010 | Shigeta et al. | |
| 2010/0170849 A1 | 7/2010 | Callan et al. | |
| 2010/0176340 A1 | 7/2010 | Callan et al. | |
| 2010/0317602 A1 | 12/2010 | Moore | |
| 2012/0006748 A1 | 1/2012 | Callan et al. | |

FOREIGN PATENT DOCUMENTS

| | | | |
|---|---|---|---|
| CA | 2129991 A1 | 7/1994 | |
| CN | 85107296 A | 4/1987 | |
| CN | 101015501 | 8/2007 | |
| EP | 1849466 | 1/2012 | |
| JP | 2002-045420 A | 2/2002 | |
| JP | 2005330244 | 12/2005 | |
| JP | 2007056013 A | 3/2007 | |
| JP | 2007-137836 A | 6/2007 | |
| WO | WO 82/03773 A1 | 11/1982 | |
| WO | WO 99/20249 A1 | 4/1999 | |
| WO | WO 03/009828 A1 | 2/2003 | |
| WO | WO 2007058498 A1 * | 5/2007 | A61K 31/195 |
| WO | WO 2007/121807 A1 | 11/2007 | |
| WO | WO 2010/055963 A1 | 5/2010 | |

OTHER PUBLICATIONS

Pentec Health (Abs. from Journal of Renal Nutrition (Mar. 2011) 21 (2): 207, attached to facsimile provided by Applicant), 1 page.*
Allwood et al, Compatibility and Stability of Additives in Parenteral Nutrition Admixtures, (Review Article), Nutrition (1998), vol. 14, No. 9, pp. 697-706 (10 pages).*
Friedman et al., The Amino Acid-Sugar Reaction, J. Biol. Chem. (1950), 184:599-606 (9 pages).*
Fry et al, Formation of Maillard Reaction Products in Parenteral Alimentation Solutions, The Journal of Nutrition (1982), vol. 112, pp. 1631-1637 (7 pages).*
Göğüş et al, Kinetics of Maillard Reactions Between the Major Sugars and Amino Acids of Boiled Grape Juice, Lebensm.-Wiss.u.-Technol., 31, 196-200 (1998) (5 pages).*
Martins et al, Kinetics of the glucose/glycine Maillard reaction pathways: influences of pH and reactant initial concentrations, Food Chemistry 92 (2005) 437-448. (12 pages).*
Mirtallo et al, Special Report: Safe Practices for Parenteral Nutrition, Journal of Parenteral and Enteral Nutrition (Suppl., 2004) vol. 28, No. 6, pp. S 39-S 70 (32 pages).*

(Continued)

*Primary Examiner* — Brian-Yong Kwon
*Assistant Examiner* — Miriam A Levin
(74) *Attorney, Agent, or Firm* — Stradley Ronon Stevens & Young, LLP

(57) ABSTRACT

The invention provides intradialytic parenteral nutrition (IDPN) solutions with low carbohydrate for the treatment of malnutrition in dialysis patients. The IDPN solutions of the invention are particularly advantageous for the treatment of malnutrition in patients who are diabetic or suffer from other glucose management related pathologies or patients who require strict fluid management.

43 Claims, No Drawings

(56) References Cited

OTHER PUBLICATIONS

Remington (The Science and Practice of Pharmacy, 21st ed. (2005), Chap. 42, Intravenous Administration, pp. 837-849) (16 pages total).*
PDR (Physician's Desk Reference, Aminosyn II, Human Prescription Drug Label, (Ver. 15, Mar. 2014; Rev. date of cited information—Mar. 2008) (19 pages).*
Moore and Lindenfeld (Intradialytic Parenteral Nutrition: A Nutritional Support Intervention for High-Risk Malnutrition in Chronic Kidney Disease, Support Line: a newsletter for Dietitians; a Publication of Dietitians in Nutrition Support, vol. 29, No. 5 (Oct. 2007), pp. 6-16) (11 pages).*
Koretz, An essential infusion for an essential organ, Nutrition in Clinical Practice (Aug. 2011) 26 (4): pp. 434-439, excerpt only, 1 page.*
Pumin et al., Nutritional Supplementation Acutely Increases Albumin Fraction Synthetic Rate in Chronic Hemodialysis Patients, J Am Soc Nephrol (2004) 15: 1920-1926.*
Abbas, et al. Biochemical nutritional parameters and their impact on hemodialysis efficiency. Saudi J Kidney Dis Transpl. 2009; 20(6):1105-1109.
International search report and written opinion dated Feb. 28, 2011 for PCT Application No. US10/03192.
Kalantar-Zadeh, et al. A Malnutrition-Inflammation Score is Correlated With Morbidity and Mortality in Maintenance Hemodialysis Patients. American Journal of Kidney Diseases. 2001; 38(6):1251-1263.
Charra, et al. Volume control, blood pressure and cardiovascular function. Lesson from hemodialysis treatment. Nephron Physiol. 2003;93(4):p. 94-101.
Dezfuli, et al. Severity of hypoalbuminemia predicts response to intradialytic parenteral nutrition in hemodialysis patients. J Ren Nutr. Jul. 2009;19(4):291-7.
Dukkipati, et al. Is there a role for intradialytic parenteral nutrition? A review of the evidence. Am J Kidney Dis. Feb. 2010;55(2):352-64. Epub Oct. 25, 2009.
Fliser, et al. Insulin resistance and renal disease. Contrib Neprhol 2006; 151:203-11.
Guarnieri, et al. Insulin resistance in chronic uremia J Ren Nutr. Jan. 2009;19(1):20-4.
Guarnieri, et al. Mechanisms of malnutrition in uremia. Kidney Int Suppl. Nov. 1997; 62: 541-44.
International search report and written opinion dated Sep. 27, 2010 for PCT Application No. US10/43944.
International search report and written opinion dated Mar. 9, 2010 for PCT Application No. US2009/049800.
Miller. Commercial premixed parenteral nutrition: Is it right for your institution? Nutr Clin Pract. Aug.-Sep. 2009;24(4):459-69.
Moore, et al. Intradialytic Parenteral Nutrition: A Nutrition Support Intervention for High-risk Malnutrition in Chronic Kidney Disease. Support Line. 2007; 29(5): 6-16.
Moore. Challenges of nutrition intervention for malnourished dialysis patients. J Infus Nurs. Nov.-Dec. 2008;31(6):361-6.
Nesrallah, et al. Can extracelluar fluid vol. expansion in hemodialysis patients be safely reduced using the hemocontrol biofeedback algorithm? A randomizxed Trial ASAIO I. May-Jun. 2008;54(3):270-4.
Nesrallah, et al. Volume control and blood pressure management in patients undergoing quotidian hemodialysis Am J Kidney Dis. Jul. 2003;42(1 Suppl):13-7.
Raimann, et al. Consequnces of overhydration and the need for dry weight assessment. Contrib Nephrol. 2008;161:99-107.
Shinohara, et al. Insulin resistance as an independent predictor of cardiovascular mortality in patients with end-stage renal disease. J Am Soc Nephrol. Jul. 2002; 13 (7): 1894-900.
Smolle, et al. Intradialytic parenteral nutrition in malnourished patients on chronic haemodialysis therapy. Nephrol Dial Transplant. 1995;10(8):1411-6.
Svensson, et al. Insulin resistance in diabetic nephropathy—cause or consequence? Diabetes Metab Res Rev Sep.-Oct. 2006; 22(5): 401-410.
Warady, et al. KDOQI clinical practice guideline for nutrition in children with CKD: 2008 update. Supplemental to AJKD. Mar. 2008; 53(3), suppl 2.
Wolfsheimer. Problems in diabetes mellitus management. Insulin resistance. Probl Vet Med. Dec. 2, 1990(4): 591-601.
Wystrychowski, et al. Dry Weight' sine qua non of adequate dialysis. Adv Chronic Kidney Dis. Jul. 2007;14(3):el 0-6.
Yokoyama, et al. Dialysis staff encouragement and fluid control adherence inpatients on hemodialysis. Nephrol Nurs J. May-Jun. 2009;36(3):289-97.
Zhang, et al. Kidney Disease and the metabolic syndrome. Am J Med Sci Dec. 2005; 330 (6):319-25.
Baxter Healthcare. Nutrineal Product Label Information. Aug. 5, 2005.
Goldstein, et al. Intradialytic Paretneral Nutrition "Evolution and Current Concepts. Journal of Rena Nutrition,"; vol. 1(1) January; 1991: pp. 9-22.
Canepa, et al. Acute effects of simultaneous intraperitoneal infusion of glucose and amino acids. Kidney Int. May 2001;59(5):1967-73.
Christianson, et al. Determinants of insulin availability in parenteral nutrition solutions. JPEN J Parenter Enteral Nutt. Jan.-Feb. 2006;30(1):6-9.
Garibotto, et al. Acute effects of peritoneal dialysis with dialysates containing dextrose or dextrose and amino acids on muscle protein turnover in patients with chronic renal failure. J Am Soc Nephrol. Mar. 2001;12(3):557-67.
Marshall, et al. Glycemic control in diabetic CAPD patients assessed by continuous glucose monitoring system (CGMS). Kidney Int. Oct. 2003;64(4):1480-6.
Moore, et al. Challenges of providing nutrition support in the outpatient dialysis setting. Nutr Clin Pract. Apr. 2005;20(2):202-12.
Tjiong, et al. Dialysate as food: combined amino acid and glucose dialysate improves protein anabolism in renal failure patients on automated peritoneal dialysis. J Am Soc Nephrol. May 2005;16(5):1486-93. Epub Mar. 30, 2005.
Office action dated Nov. 8, 2011 for U.S. Appl. No. 12/847,513.
U.S. Appl. No. 13/541,604, filed Jul. 3, 2012, Moore.
Brem, et al. Use of amino acid peritoneal dialynate for one year in a child on CCPD Perit Dial Int. Nov.-Dec. 1996;16(6):634-6.
Chertow, et al. Laboratory Surrogates of Nutritional Status After Administration of Intraperitoneal Amino Acid-Based Solutions in Ambulatory Peritoneal Dialysis Patients. Journal of Renal Nutrition. 1995; 5(3):116-123.
Delarue, et al. Effects of an amino acid dialysate on leucine metabolism in continuous ambulatory peritoneal dialysis patients. Kidney Int. Nov. 1999;56(5):1934-43.
Dibble, et al. Amino-acid-based continuous ambulatory perioneal dialysis (CAPD) fluid over twelve week: effects on carbohydrate and lippd metabolism. Perit Dial Int 1990;10(1):71-7.
Dombros, et al. Six-month overnight intraperitoneal amino-acid infusion in continuous ambulatory peritoneal dialysis (CAPD) patients—no effect on nutritional status. Perit Dial Int 1990;10(1):79-84.
Faller, et al. Clinical evaluation of an optimized 1.1% amino-acid solution for peritoneal dialysis. Nephrol Dial Transplant. 1995;10(8):1432-7.
Jones, et al. Treatment of malnutrition with 1.1% amino acid peritoneal dialysis solution: results of a multicenter outpatient study. Am J Kidney Dis. Nov. 1998;32(5):761-9.
Kopple, et al. Treatments of malnourished CAPD patients with an amino acid based dialysate. Kidney Int. Apr. 1005;47(4): 1148-57.
Li, et al. A 3-year, prospective, randomized, controlled study on amino acid dialysate in patients on CAPD. American Journal of Kidney Diseases. 2003:42(1):173-183.
Olszowska, et al. Peritoneal transport in peritoneal dialysis patients using glucose-based and aminio acid-based solutions. Perit Dial Int. Sep.-Oct. 2007;27(5):544-53.
Park, et al. Peritoneal transport dusing dialysis with amino acid-based solutions. Perit Dial Int. 1993;13(4):280-8.
Taylor, et al. Long-term use of 1.1% amino acid dialysis solition in hypoalbuminemia continuous ambulatory perinoteal dialysis patients. Clin Nephrol. Dec. 2002;5(6):445-50.

(56) References Cited

OTHER PUBLICATIONS

William, et al. Amino Acid Absorption Following Instraperitoneal Administration in CAPD Patients. Perit Dial Int. Jul./Sep. 1982;2(3):121-130.
Cherry, et al. Efficacy of intradialytic parenteral nutrition in malnourished hemodialysis patients. Am J Health Syst Pharm. Sep. 15, 2002;59(18):1736-41.
Krause, et al. Intradialytic parenteral nutrition in malnourished children treated with hemodialysis. J Ren Nutr. Jan. 2002;12(1):55-9.
McCann, et al. Effect of intradialytic parenteral nutrition on delivered Kt/V. Am J.Kidney Dis. Jun. 1999;33(6):1131-5.
Vassalotti, J.A. "Nutritional Strategies for the Patient with Diabetic Nephropathy" Chapter 10 of Nutritional Strategies for the Diabetic/Prediabetic Patient, Editor: Mechanick, J.I., 2006, pp. 149-169.
Lowrie, Edmund G., et al., "Death Risk in Hemodialysis Patients: The Predictive Value of Commonly Measured Variables and an Evaluation of Death Rate Differences Between Facilities", Am. J. Kidney Disease, vol. XV, No. 5 May 1990, pp. 458-482.
Lacson, Eduardo, Jr., "Potential Impact of Nutritional Intervention on End-Stae Renal Disease Hospitalization, Death, and Treatment Costs", J. Renal Nutrition, vol. 17, No. 6 Nov. 2007, pp. 363-371.
Mortelmans, Anna Katharina, et al., "Intradialytic Parenteral Nutrition in Malnourished Hemodialysis Patients: A Prospective Long-Term Study", J. Parenteral and Enteral Nutrition, vol. 23, No. 2 (1999), pp. 90-95.
Dukkipati, Ramanath, et al., "Is There a Role for Intradialytic Parenteral Nutrition? A Review of the Evidence", Am. J. Kidney Dis., Feb. 2010; 55(2), pp. 352-364.
Feinfeld, Donald A., et al., "Massive and disproportionate evaluation of blood urea nitrogen in acute azotemia", International Urology and Nephrology, vol. 34 (2002), pp. 143-145.
Klein, Catherine J., et al., "Overfeeding macronutrients to critically ill adults: Metabolic complications", J. Am. Dietetic Assoc., vol. 98, No. 7 Jul. 1998, pp. 795-806.
Rollins, Carol J., "Peripheral Parenteral Nutrition", MVI Newslines, pp: 1-6.
Moore, Eileen, et al., "A Superior Proprietary IDPN Formulation for Malnourished Patients with Diabetes", J. Renal Nutrition, vol. 21, Issue 2 Mar. 2011, pp. 205-210.
Mirtallo, Jay, et al., "Safe Practices for Parenteral Nutrition", J. Parenteral and Enteral Nutrition, vol. 28, No. 6 Nov.-Dec. 2004, pp. S39-S71.
Nordfjeld, K., et al., "Storage of Mixtures for Total Parenteral Nutrition—Long-Term Stability of a Total Parenteral Nutrition Mixture", J. Clinical and Hospital Pharm., vol. 8 (1983), pp. 265-274.
Gura, Kathleen M., "Is There Still a Role for Peripheral Parenteral Nutrition", Nutrition in Clinical Practice, vol. 24, No. 6 Dec./Jan. 2009, pp. 709-717.
Gazitua, Ricardo, et al., "Factors Determining Peripheral Vein Tolerance to Amino Acid Infusions", Arch. Surg., vol. 114 Aug. 1979, pp. 897-900.
Culebras, Jesus M., et al., "Practical aspects of peripheral parenteral nutrition", Curr. Opin. Clin. Nutr. Metab. Care, vol. 7, pp. 303-307.
Doellman, Darcy, et al., "Infiltration and Extravasation: Update on Prevention and Management", J. Infusion Nursing, vol. 32, No. 4 Jul./Aug. 2009, pp. 203-211.
Product Label: Aminosyn II 15% (An Amino Acid Injection, Sulfite-Free), Hospira, Inc.
Harju, et al., "A high amount of branched chain amino acids did not change favorable plasma albumin and protein concentrations during 48 hours postlaprotomy infusion—an experimental stody in the rabbit", Z. exp Chir. Transplant kunstl organe (1986) vol. 19, pp. 28-35.
Werynsky, et al., "Comparison of kinetic characteristics of amino acid-based and dipeptide-based peritoneal dialysis solutions", The International Journal of Artificial Organs (2006) vol. 29, No. 7, pp. 661-690.

Madigan, et al., "Effectiveness of intradialytic parenteral nutrition in diabetic patients with end-stage renal disease", J. Amer. Diabetic Assoc., 90.6 (Jun. 1990); p. 861-3.
Yarandi, SS, et al., "Amino acid composition in parenteral nutrition: what is the evidence?", Curr. Opin. Clin. Nutr. Metab. Care, Jan. 2011; 14(1):75-82.
Mehrotra, R., et al., "Nutritional Management of Maintenance Dialysis Patients: Why Aren't We Doing Better?", Annu. Rev. Nutr., 21:343-379.
Abel, RM, et al., "Intravenous essential L-amino acids and hypertonic dextrose in patients with acute renal failure. Effects on serum potassium, phosphate, and magnesium", Am. J. Surg., Jun. 1972; 123(6):632-638.
National Kidney Foundation. K/DOQI Clinical Practice Guidelines for Nutrition in Chronic Renal Failure. American Journal of Kidney Diseases 2000; 35(suppl. 2):S1-S140.
Pentech Infusions Manual, "Intraperitoneal Nutrition and the Amino-PD Program", 1987.
Dickerson, et al., "Net protein anabolism with hypocaloric parenteral nutrition in obese stressed patients", Am. J. Clin. Nutr., 1986;44:747-755.
Baxter Healthcare Corporation, 20% ProSol—sulfite-free (Amino Acid) Injection, Pharmacy Bulk Package Not for Direct Infusion in Vlaflex Plastic Container, Product Information, 1997, 10 pgs.
Beddhu, et al. Inflammation and inverse associations of body mass index and serum creatinine with mortality in hemodialysis patients. J Ren Nutr. Nov. 2007;17(6):372-80.
Gilbertson, et al. Projecting the number of patients with end-stage renal disease in the United States to the year 2015. J Am Soc Nephrol. Dec. 2005;16(12):3736-41. Epub Nov. 2, 2005.
Ikizler. Nutrition support for the chronically wasted or acutely catabolic chronic kidney disease patient. Semin Nephrol. Jan. 2009;29(1):75-84. doi: 10.1016/j.semnephrol.2008.10.011.
Kalantar-Zadeh, et al. Revisiting mortality predictability of serum albumin in the dialysis population: time dependency, longitudinal changes and population-attributable fraction. Nephrol Dial Transplant. 2005; 20:1880-1888.
Kaysen, et al. Trends and outcomes associated with serum albumin concentration among incident dialysis patients in the United States. J Ren Nutr. Jul. 18, 2008(4):323-31. doi: 10.1053/j.jrn.2008.04.002.
McCowen, et al. Hyperglycemia and nutrition support: theory and practice. Nutr Clin Pract. Jun. 2004;19(3):235-44.
National Kidney Foundation. K/DOQI Clinical Practice Guidelines for Nutrition in Chronic Renal Failure. Am J Kidney Dis. Jun. 2000;35(6 Suppl 2):S1-140.
Office action dated Aug. 17, 2012 for U.S. Appl. No. 12/847,513.
Powers. Considerations in the use of 3:1 intradialytic parenteral nutrition solutions containing long-chain triglyceride. Contemporary Dialysis and Nephrology. Feb. 1990; 11(2):29-37.
Pupim, et al. Intradialytic parenteral nutrition improves protein and energy homeostasis in chronic hemodialysis patients. J Clin Invest. Aug. 2002;110(4):483-92.
Pupim, et al. Nutritional supplementation acutely increases albumin fractional synthetic rate in chronic hemodialysis patients. J Am Soc Nephrol. Jul. 2004;15(7):1920-6.
Takano. Fluid therapy in diabetic patients. 1994; 168(5):443-447. (in Japanese with machine English translation).
United States Renal Data System. (2007). Incidence and Prevalence. Retrieved Aug. 14, 2008 from www.usrds.org/2007/pdf/02_incid_prev_07.pdf.
United States Renal Data System. (2007). Patient Characteristics. Retrieved Aug. 14, 2008 from www.usrds.org/2007/pdf/03_pt_char_07.pdf.
Waxman, et al. Safety and efficacy of glycerol and amino acids in combination with lipid emulsion for peripheral parenteral nutrition support. JPEN J Parenter Enteral Nutr. Jul.-Aug. 1992;16(4):374-8.
Tjiong, et al. Peritoneal dialysis with solutions containing amino acids plus glucose promotes protein synthesis during oral feeding. Clin J Am Soc Nephrol. Jan. 2007;2(1):74-80. Epub Nov. 8, 2006.

\* cited by examiner

NUTRITIVE COMPOSITIONS AND METHODS OF USING SAME

RELATED APPLICATIONS

This application claims the benefit of U.S. Provisional Application Nos. 61/078,636, filed on Jul. 7, 2007, and 61/080,567, filed on Jul. 14, 2008, the entire contents of each are incorporated herein by reference in their entireties.

FIELD OF THE INVENTION

The invention pertains to nutrition supplement compositions for patients receiving dialysis treatment and methods of using the nutrition supplement compositions. The nutrition supplement compositions include reduced levels of carbohydrates and lower volume to reduce complications in patients who are diabetic or suffer from other glucose management related pathologies, or patients who require strict fluid management.

BACKGROUND OF THE INVENTION

Severe malnutrition remains a problem for patients receiving maintenance hemodialysis (MHD). Dialysis patients often have poor appetites and low energy. This malnutrition is reflected in low serum albumin concentrations, a strong predictor of increased morbidity and mortality. (Moore and Lindenfield, *Support Line* 29(5):7-16 (October 2007)). Patients are often treated using diet liberalization, oral supplements and enteral feeding. When these methods are not effective intradialytic parenteral nutrition (IDPN) may be utilized for more aggressive nutrition repletion efforts.

IDPN is infused during the hemodialysis procedure. IDPN has been used for decades and has resulted in weight gain and improved protein levels in patients. (U.S. Publication No. 2005/0148647). The typical IDPN treatment delivers 4-6 mg/kg/minute of glucose for patients in need of carbohydrate control and 6-8 mg/kg/minute for patients who do not need carbohydrate control. Blood glucose must be monitored to avoid problems associated with insulin resistance, hyperglycemia and hypoglycemia. In some cases, insulin is also administered either in the IDPN solution or more typically separately administered subcutaneously to modulate blood glucose levels. IDPN generally contains 1.2-1.4 g/kg of amino acids. However, these amounts can be lowered for patients who do not tolerate protein well. Monitoring of serum bicarbonate and carbon dioxide levels must be monitored to check for acidosis caused by administration of amino acids. Lipids are provided in IDPN at a rate between 4 mg/kg/minute and 12-12.5 g/hour depending on tolerance of the lipids by the patient. Generally, these lipids are emulsions of purified vegetable oil from soybean (Intraliipid® from Kabi Vitrum or Travamulsion® from Travenol) or safflower oil (Liposyn® from Abbott). (Powers, *Contemporary Dialysis and Nephrology:*29-31 (February 1990).

IDPN is usually administered in one liter of solution, and occasionally micronutrients, like vitamins and minerals are co-administered in or with IDPN. IDPN has proved effective in decreasing morbidity and mortality in MHD patients, leads to increased levels of serum albumin and creatine levels, and increased body weight. (Moore and Celano, *Nutrition in Clinical Practice,* 20(2):202-212 (2005)). Hypoglycemia is another potential dangerous result of the administration of insulin during IDPN with symptoms of nervousness, sweating, intense hunger, trembling, weakness, palpitations, and trouble speaking.

Problems associated with IDPN include hyperglycemia, complications in patients with insulin resistance or other problems associated with glucose management, as well as complications in patients who require strict fluid management. The glucose concentrations administered with IDPN can cause hyperglycemia and hypoglycemia in some patients. The administration of insulin can sometimes successfully treat this hyperglycemia, but some patients demonstrate insulin resistance, and may not respond to insulin treatment. (Goldstein and Strom, *Journal of Renal Nutrition* 1(1):9-22 (January 1991)). Hyperglycemia is a major barrier to effective nutrition support even outside the context of hemodialysis. Many studies report associations between hyperglycemia and increased morbidity and mortality. (McCowen and Bistrian, *Nutrition in Clinical Practice,* 19(3):235-244 (June 2004)). Moreover, the amount of fluid in typical IDPN treatment is a barrier to use in patients with strict fluid management. Thus, a need exists for an improved IDPN composition for administration to patients that diminishes hyperglycemia associated with IDPN administration and decreases the need for the administration of insulin with IDPN. Moreover, a need exists for a lower volume IDPN dosage form.

SUMMARY OF THE INVENTION

The invention provides intradialytic parenteral nutrition (IDPN) solutions with low carbohydrate content and low volume. The IDPN solutions of the invention are effective in the treatment of malnutrition in patients receiving dialysis treatment. These solutions also reduce the need for insulin administration when administered to patients undergoing maintenance hemodialysis (MHD) patients. Moreover, patients with metabolic conditions that impair their glucose tolerance and metabolism would also benefit from the IDPN solutions of the invention. Also, patients with strict fluid management would benefit from the IDPN solutions of the invention. The IDPN solutions of the invention also include amino acids and, optionally, lipids and/or micronutrients such as vitamins, trace elements and/or minerals. In certain preferred embodiments the IDPN solutions are lipid free. In other preferred embodiments, the IDPN solutions of the invention are kept in containers for administration to patients, such as bags appropriate for parenteral administration. In one embodiment, each bag contains one dose of IDPN for a patient. In other embodiments, these doses are supplemented with pharmaceuticals, such as insulin. These doses are often administered subcutaneously using a separate administration system.

DETAILED DESCRIPTION

The invention provides intradialytic parenteral nutrition (IDPN) solutions with low carbohydrate and low volume. The IDPN solutions of the invention allow medical personnel to engage in reduced carbohydrate management for MHD patients when they receive IDPN. Moreover, the IDPN solutions of the invention are particularly effective for treating malnutrition in MHD patients who have glucose management difficulties including patients that are insulin resistant, who have type I diabetes or pancreatitis. Also, the reduction of carbohydrate in the IDPN solutions of the invention favors anabolism over catabolism, thus effectively treating malnutrition. In preferred embodiments, the IDPN solutions of the invention have reduced volume, so as to reduce side effects associated with high infusion volumes including dyspnea, increased respiratory rate, rhonchi edema, hypertension, and anxiety. The IDPN solutions of the invention are especially appropriate for patients that have adequate caloric intake but not protein intake. Further, the IDPN solutions of the invention can be administered to normal weight or obese patients.

Preferably, the IDPN solutions of the invention contain carbohydrate and amino acids. In some embodiments of the IDPN solution of the invention, the solution also contains lipids. In other embodiments of the IDPN solution of the invention, the solution also contains micronutrients such as vitamins, trace elements and/or minerals. In other embodiments of the IDPN solution of the invention, the solution also contains pharmaceuticals such as insulin. In preferred embodiments, of the IDPN solution of the invention, pharmaceuticals are coadministered with the IDPN, but are not part of the IDPN solution. For example, insulin can be administered subcutaneously in a separate injection. Preferably, the carbohydrate contained in the IDPN solutions of the invention dextrose (D-glucose). The amino acids contained in the IDPN solutions of the invention include combinations of two or more of the standard 20 amino acids. Preferably, all 20 of the amino acids are administered in the IDPN solutions of the invention. More preferably, 17 amino acids are used. Preferably, the solution of amino acids used to make the IDPN solution of the invention is a concentrated solution and is used in the invention due to the benefits of low volume. Preferably the concentrated solution contains 15 g/mL of amino acids. More preferably, the concentrated solution contains 20 g/mL of amino acids.

Preferably, the IDPN solutions of the invention contain between 0.02 and 0.10 g/mL of dextrose in solution. Preferably, the IDPN solutions of the invention contain between 0.04 and 0.08 g/mL of dextrose in solution. More preferably, the IDPN solutions of the invention contain between 0.05 and 0.07 g/mL of dextrose in solution. More preferably the IDPN solutions of the invention contains between 0.055 and 0.065 g/mL of dextrose in solution. In various embodiments of the IDPN solutions of the invention, the solutions contain 0.02, 0.03, 0.04, 0.05, 0.06, 0.07, 0.08, 0.09 or 0.10 g/mL of dextrose in solution. In other embodiments of the IDPN solutions of the invention, the solutions contain 0.055, 0.056, 0.057, 0.058, 0.059, 0.060, 0.061, 0.062, 0.063, 0.064 or 0.065 g/mL of dextrose in solution.

Preferably, the IDPN solutions of the invention are packaged in sterile containers for administration to patients. Preferably, the sterile containers are bags used for parenteral administration of IDPN solutions to a patient. Preferably the bags hold between 100 mL of IDPN solution and 2 liters of IDPN solution. More preferably, the bags hold between 300 mL or 1 liter of IDPN solution. More preferably, the bags hold between 419 mL of IDPN solution and 809 mL of IDPN solution. More preferably, the bags hold between 350 mL and 635 mL of solution.

Preferably, the IDPN solutions of the invention are packaged in sterile containers so that the sterile container holds one dose of IDPN solution for administration to a patient. Preferably the dose of IDPN solution has a volume between 100 mL of IDPN solution and 2 liters of IDPN solution. More preferably, the dose of IDPN solution has a volume between 350 mL and 635 mL of IDPN solution. More preferably, the dose of IDPN solution has a volume of 300, 342, 350, 383, 400, 419, 427, 450, 483, 500, 540, 550, 600, 613, 635, 700 or 809 mL. In conjunction with a volume associated with the IDPN solution of the invention, the term "about" means+/− 10 mL per dose.

Preferably, a dose of the IDPN solution of the invention contains between 10 and 50 g of dextrose. More preferably, a dose of the IDPN solution contains between 20 and 45 g of dextrose. More preferably, a dose of the IDPN solution contains 20, 23, 26, 30, 35 and 41 g of dextrose. In conjunction with an amount of dextrose associated with the IDPN solution of the invention, the term "about" means+/−1 g per dose.

In some embodiments of the IDPN solution of the invention, the amount of dextrose in the IDPN solution is dependent upon the mass of the patient receiving the IDPN treatment. Generally, the IPDN solution of the invention contains a dose of dextrose less than 1 g/kg of body mass of the patient. For example, a patient with a mass between 34 and 39 kg would receive an IDPN solution containing 20 g of dextrose, a patient with a body mass between 40 and 44 kg would receive an IDPN solution containing 23 g of dextrose, a patient with a body mass between 45 and 51 kg would receive an IDPN solution containing 26 g of dextrose, a patient with a body mass between 52 and 59 kg would receive an IDPN solution containing 30 g of dextrose, a patient with a body mass between 60 and 69 kg would receive an IDPN solution containing 35 g of dextrose, and a patient with a body mass of 70 kg, or greater, would receive an IDPN solution containing 41 g of dextrose Preferably, the IDPN solutions of the invention contain between 0.10 and 0.20 g/mL of amino acids in solution. Preferably the IDPN solutions of the invention contain between 0.12 and 0.18 g/ml of amino acids in solution. More preferably the IDPN solutions of the invention contains between 0.15 and 0.17 g/mL of amino acids in solution. In various embodiments of the IDPN solutions of the invention, the solutions contain 0.10, 0.11, 0.12, 0.13, 0.14, 0.15, 0.16, 0.17, 0.18, 0.19 or 0.20 g/mL of amino acids in solution. In other embodiments of the IDPN solutions of the invention, the solutions contain 0.150, 0.151, 0.152, 0.153, 0.154, 0.155, 0.156, 0.157, 0.158, 0.159, 0.160, 0.161, 0.162, 0.163, 0.164, 0.165, 0.166, 0.167, 0.168, 0.169 or 0.170 g/mL of amino acids in solution.

Preferably, a dose of the IDPN solution of the invention contains between 30 and 120 g of amino acids. More preferably, a dose of the IDPN solution contains between 51 and 110 g of amino acids. More preferably, a dose of the IDPN solution contains 50, 52, 52.5, 55, 60, 65, 68, 70, 75, 78, 80, 85, 90, 95, 100, 105 and 110 g of amino acids. In conjunction with an amount of amino acids associated with the IDPN solution of the invention, the term "about" means+/−3 g per dose.

In some embodiments of the IDPN solution of the invention, the amount of amino acids in a dose of the IDPN solution is dependent upon the mass of the patient receiving the IDPN treatment. For example, a patient with a body mass between 34 and 39 kg would receive an IDPN solution containing 51 g of amino acids, a patient with a body mass between 40 and 44 kg would receive an IDPN solution containing 60 g of amino acids, a patient with a body mass between 45 and 51 kg would receive an IDPN solution containing 68 g of amino acids, a patient with a body mass between 52 and 59 kg would receive an IDPN solution containing 78 g of amino acids, a patient with a body mass between 60 and 69 kg would receive an IDPN solution containing 90 g of amino acids, and a patient with a body mass of 70 kg, or greater, would receive an IDPN solution containing 105 g of amino acids.

In some embodiments of the IDPN solution of the invention, the solution also contain lipids. Preferably the lipids are emulsions of purified vegetable oil from soybean (Intralipid® from Kabi Vitrum or Travamulsion® from Travenol) or safflower oil (Liposyn® from Abbott). IDPN solutions of the invention with lipids contain 5-30% lipid by volume. Preferably, IDPN solutions of the invention with lipids contain 10-20% lipid by volume. Lipids should not be added to IPDN solutions administered to patients with hyperlipemia, acute pancreatitis, lipid nephrosis or allergic reactions to eggs.

In preferred embodiments of the IDPN solution of the invention, the solution is lipid free.

In some embodiments of the IDPN solution of the invention, the solution also contains micronutrients such as vitamins, trace elements and/or minerals. Vitamins and minerals that are optionally added to the IDPN solutions of the invention include water soluble vitamins such as vitamin C, folic acid, vitamin $B_1$, and vitamin $B_6$, as well as multivitamins lacking vitamin K, and trace elements such as zinc, selenium, copper, chromium, and manganese. Minerals also include mineral salts such as sodium phosphate, and magnesium sulfate.

In some embodiments of the IDPN solution of the invention, the solution also contains pharmaceutical compositions. One example of a pharmaceutical composition appropriate for inclusion in the IPDN solution of the invention is insulin. In some embodiments, insulin is added to the IDPN solution just prior to administration to the patient, because many solution container materials will absorb insulin. Preferably, insulin is coadministered independent of the IDPN solution. For example, the insulin can be subcutaneously injected during treatment with IDPN. Preferably 5-20 units of insulin is added with one dose of IDPN.

Preferably, the IDPN solution of the invention is administered to dialysis patients who are suffering from malnutrition. A dialysis patient suffering from malnutrition can be identified by detecting evidence of protein or energy malnutrition and inadequate dietary protein intake, evidence of the inability to administer or tolerate adequate oral nutrition inclusive of supplements and tube feeding, and evidence that the combination or oral and/or enteral intake when combined with IDPN will meet the patient's nutritional needs.

Administration of the IDPN solution of the invention generally coincides with the start of hemodialysis on a patient. During IDPN solution administration the patient should be monitored for glucose tolerance, protein status and/or fat status. Glucose monitoring includes blood glucose level before, during and after IDPN administration and monitoring the patient for symptoms of hyper or hypoglycemia. The symptoms of hyperglycemia include nausea, thirst, headache, vomiting and weakness. The symptoms of hypoglycemia include headache, dizziness, tremors, cold sweat, confusion, and faintness. The presence of hyper or hypoglycemia can then be confirmed through blood sugar analysis, such as via a fingerstick or arterial glucose level. To treat hyperglycemia, insulin is administered. To treat hypoglycemia the patient should receive 20-30 g of simple carbohydrates orally. Protein monitoring includes the monitoring of blood urea nitrogen (BUN) prior to dialysis and Kt/V which is a measure of dialysis adequacy.

Fat monitoring includes a pre-dialysis triglyceride test prior to lipid infusion and then another following first lipid infusion to ensure that the patient is clearing lipids from the bloodstream. Also, sodium, potassium, phosphorus and magnesium levels should be monitored for the presence of refeeding syndrome.

Generally, the IDPN solution of the invention is administered through a port post dialyzer of the dialysis machine being used to perform hemodialysis on the patient. In a preferred embodiment, the IDPN infusion is performed through the venous chamber of the dialysis machine. Examples of routes of parenteral administration include intravenous, intradermal, subcutaneous, and intraperitoneal administration. Any pharmaceutically acceptable carrier can be used in conjunction with the IDPN solution of the invention. The IDPN solution of the invention can be administered in the same manner prior art IDPN solutions have been administered.

EXAMPLES

Protein Repletion Formulas

The following IDPN formulas were developed. These formulas are administered to a MHD patient requiring 3.25 hours or longer dialysis treatment time. The formulas are fat free and micronutrient free, but these components could easily be added.

TABLE 1

| WEIGHT | CHO | AA | VOL | Total Kcals | FINAL (g/dl) |
|---|---|---|---|---|---|
| 34-39 Kg | 29 ml | 255 ml | (Approx. 50 cc | 272 kcals | D5.9 |
|  | 20 gm | 51 gm | fill) 334 ml |  | 15.3AA |
| 40-44 Kg | 33 ml | 300 ml | 383 ml | 318 kcals | D6.0 |
|  | 23 gm | 60 gm |  |  | 15.7AA |
| 45-51 Kg | 37 ml | 340 ml | 427 ml | 360 kcals | D6.1 |
|  | 26 gm | 68 gm |  |  | 15.9AA |
| 52-59 Kg | 43 ml | 390 ml | 483 ml | 414 kcals | D6.2 |
|  | 30 gm | 78 gm |  |  | 16.1AA |
| 60-69 Kg | 50 ml | 450 ml | 550 ml | 479 kcals | D6.4 |
|  | 35 gm | 90 gm |  |  | 16.4AA |
| 70+ Kg | 59 ml | 525 ml | 635 ml | 560 kcals | D6.5 |
|  | 41 gm | 105 gm |  |  | 16.6AA |

The infusion rate schedule for subjects of each weight class are shown in Table 2, below.

TABLE 2

| Weight class | Week 1 Infusion Rate | Week 2 Infusion Rate |
|---|---|---|
| 34-39 kg | 50 mL/hour | 105 mL/hour |
| 40-44 kg | 60 mL/hour | 120 mL/hour |
| 45-51 kg | 65 mL/hour | 135 mL/hour |
| 52-59 kg | 75 mL/hour | 150 mL/hour |
| 60-69 kg | 85 mL/hour | 170 mL/hour |
| 70+ kg | 100 mL/hour | 195 mL/hour |

The following formulations were made with a more dilute commercially available source of amino acids.

TABLE 3

| WEIGHT | CHO | AA | VOL | Total Kcals | FINAL (g/dl) |
|---|---|---|---|---|---|
| 34-39 Kg | 29 ml | 340 ml | (Approx. 50 cc | 272 kcals | D4.8 |
|  | 20 gm | 51 gm | fill) 419 ml |  | 12.2AA |
| 40-44 Kg | 33 ml | 400 ml | 483 ml | 318 kcals | D4.8 |
|  | 23 gm | 60 gm |  |  | 12.4AA |
| 45-51 Kg | 37 ml | 453 ml | 540 ml | 360 kcals | D4.8 |
|  | 26 gm | 68 gm |  |  | 12.6AA |
| 52-59 Kg | 43 ml | 520 ml | 613 ml | 414 kcals | D4.9 |
|  | 30 gm | 78 gm |  |  | 12.7AA |
| 60-69 Kg | 50 ml | 600 ml | 700 ml | 479 kcals | D5.0 |
|  | 35 gm | 90 gm |  |  | 12.9AA |
| 70+ Kg | 59 ml | 700 ml | 809 ml | 560 kcals | D5.1 |
|  | 41 gm | 105 gm |  |  | 13.0AA |

What is claimed is:

1. A method, comprising parenterally administering a sterile aqueous intradialytic parenteral nutrition (IDPN) solution to a patient in need thereof, the IDPN solution consisting essentially of between 0.05 and 0.07 g/mL of dextrose and between 0.12 and 0.18 g/mL of amino acids, wherein the solution is lipid-free and the dextrose and the amino acids are both dissolved in the same aqueous solution.

2. The method of claim 1, wherein the amino acids include combinations of two or more of the standard 20 amino acids.

3. The method of claim 1, wherein the solution consists essentially of between 0.055 and 0.065 g/mL of dextrose and between 0.12 and 0.18 g/mL of amino acids.

4. The method of claim 1, wherein the solution consists essentially of between 0.05 and 0.07 g/mL of dextrose and between 0.15 and 0.17 g/mL of amino acids.

5. The method of claim 1, wherein the solution consists essentially of between 0.055 and 0.065 g/mL of dextrose and between 0.15 and 0.17 g/mL of amino acids.

6. The method of claim 1, wherein the solution is free of vitamin B1.

7. The method of claim 1, wherein the solution is free of minerals.

8. The method of claim 4, wherein the solution is free of vitamin B1.

9. The method of claim 1, wherein the amino acids include all 20 of the standard amino acids.

10. The method of claim 1, wherein the amino acids include 17 of the standard amino acids.

11. The method of claim 1, wherein the solution has a volume between 100 mL and 2 L.

12. The method of claim 1, wherein the solution has a volume between 350 mL and 635 L.

13. The method of claim 1, wherein the solution is packaged in a sterile container.

14. The method of claim 1, wherein the solution does not induce hyperglycemia in the patient.

15. The method of claim 1, wherein the solution does not induce rhonchi edema in the patient.

16. The method of claim 1, wherein the solution does not induce dyspnea in the patient.

17. The method of claim 1, wherein the solution does not increase the respiratory rate of the patient.

18. The method of claim 1, wherein the solution does not induce hypertension in the patient.

19. The method of claim 1, wherein the solution does not induce anxiety in the patient.

20. The method of claim 1, wherein the patient is a hemodialysis patient.

21. The method of claim 3, wherein the patient is a hemodialysis patient.

22. The method of claim 4, wherein the patient is a hemodialysis patient.

23. The method of claim 5, wherein the patient is a hemodialysis patient.

24. The method of any one of claims 20-23, wherein the hemodialysis patient is diabetic.

25. The method of claim 24, further comprising administering insulin to the patient.

26. The method of claim 24, further comprising monitoring glucose tolerance in the patient.

27. The method of any one of claims 20-23, further comprising monitoring protein status in the patient.

28. The method of claim 27, wherein the patient is diabetic.

29. A method, comprising parenterally administering a sterile aqueous intradialyic parenteral nutrition (IDPN) solution to a patient in need thereof, the IDPN solution comprising between 0.05 and 0.07 g/mL of dextrose and between 0.12 and 0.18 g/mL of amino acids, wherein the solution is lipid-free and the dextrose and the amino acids are dissolved in the same aqueous solution.

30. The method of claim 29, wherein the solution comprises between 0.055 and 0.065 g/mL of dextrose and between 0.12 and 0.18 g/mL of amino acids.

31. The method of claim 29, wherein the solution comprises between 0.05 and 0.07 g/mL of dextrose and between 0.15 and 0.17 g/mL of amino acids.

32. The method of claim 29, wherein the solution comprises between 0.055 and 0.065 g/mL of dextrose and between 0.15 and 0.17 g/mL of amino acids.

33. The method of claim 29, wherein the solution, when administered to a patient in need thereof, does not induce hyperglycemia in the patient.

34. The method of claim 29, wherein the solution, when administered to a patient in need thereof, does not induce rhonchi edema in the patient.

35. The method of claim 29, wherein the solution, when administered to a patient in need thereof, does not induce dyspnea in the patient.

36. The method of claim 29, wherein the solution, when administered to a patient in need thereof, does not increase the respiratory rate of the patient.

37. The method of claim 29, wherein the solution, when administered to a patient in need thereof, does not induce hypertension in the patient.

38. The method of claim 29, wherein the solution, when administered to a patient in need thereof, does not induce anxiety in the patient.

39. The method of claim 29, wherein the patient is a hemodialysis patient.

40. The method of claim 39, wherein the hemodialysis patient is diabetic.

41. The method of claim 40, further comprising administering insulin to the patient.

42. The method of claim 40, further comprising monitoring glucose tolerance in the patient.

43. The method of any one of claims 39-41, further comprising monitoring protein statue in the patient.

* * * * *